(12) United States Patent
Jayasena et al.

(10) Patent No.: US 6,177,555 B1
(45) Date of Patent: Jan. 23, 2001

(54) HOMOGENEOUS DETECTION OF A TARGET THROUGH NUCLEIC ACID LIGAND-LIGAND BEACON INTERACTION

(75) Inventors: Sumedha Jayasena; Larry Gold, both of Boulder, CO (US)

(73) Assignee: NeXstar Pharmaceuticals, Inc., Boulder, CO (US)

( * ) Notice: Under 35 U.S.C. 154(b), the term of this patent shall be extended for 0 days.

(21) Appl. No.: 09/447,863

(22) Filed: Nov. 23, 1999

Related U.S. Application Data

(63) Continuation of application No. 09/157,206, filed on Sep. 18, 1998, now Pat. No. 5,989,823.

(51) Int. Cl.$^7$ .............................. C07H 21/04; C12Q 1/68
(52) U.S. Cl. ........................... 536/23.1; 536/24.3; 435/6; 435/7.1
(58) Field of Search ................................. 536/23.1, 24.3; 435/6, 7.1

(56) References Cited

U.S. PATENT DOCUMENTS

| | | | |
|---|---|---|---|
| 5,118,801 | 6/1992 | Lizardi et al. | 536/24.3 |
| 5,270,163 | 12/1993 | Gold et al. | 435/6 |
| 5,312,728 | 5/1994 | Lizardi et al. | 435/6 |
| 5,691,145 | 11/1997 | Pitner et al. | 435/6 |
| 5,723,323 | 3/1998 | Kauffman et al. | 435/172.3 |

FOREIGN PATENT DOCUMENTS

| | | |
|---|---|---|
| 2 183 661 | 6/1987 | (GB) . |
| WO 89/06694 | 7/1989 | (WO) . |
| WO 91/198813 | 12/1991 | (WO) . |
| WO 92/14843 | 9/1992 | (WO) . |
| WO98/04740 | 2/1998 | (WO) . |

OTHER PUBLICATIONS

Ellington & Szostak (1990) Abstacts of papers presented at the 1990 meeting on RNA Processing, Cold Spring Harbor Laboratory, Cold Spring Harbor, NY, p. 84.
Joyce (1989) Gene 82:83.
Joyce & Inoue (1989) Nucleic Acids Research 17:711.
Kinzler & Vogelstein (1989) Nucleic Acids Research 17:3645.
Kostrikis et al. (1998) Science 279:1228.
Kramer et al. (1974) J. Mol. Biol. 89:719.
Levisohn & Spiegelman (1969) Proc. Natl. Acad. Sci. USA 63:805.
Levisohn & Spiegelman (1968) Proc. Natl. Acad. Sci. USA 60:866.
Nyren et al. (1993) Analytical Biochem. 208:171.
Oliphant et al. (1989) Mol. Cell. Biol. 9:2944.
Oliphant & Struhl (1988) Nucleic Acids Research 16:7673.
Oliphant & Struhl (1987) Methods in Enzymology 155:568.
Oliphant et al. (1986) Gene 44:177.
Robertson & Joyce (1990) Nature 344:467.
Szostak (1988) "Structure and Activity of Ribozymes," in *Redesigning the Molecules of Life*, (S.A. Benner ed.) Springer–Verlag Berlin Heidelberg, pp.87–113.
Theisen & Bach (1990) Nucleic Acids Research 18:3203.
Tyagi et al. (1998) Nature Biotechnology 16:49.
Tyagi and Kramer (1996) Nature Biotechnology 14:303.

*Primary Examiner*—Kenneth R. Horlick
(74) *Attorney, Agent, or Firm*—Swanson & Bratschun, LLC

(57) ABSTRACT

The presence of a target in a test mixture or the concentration of such target can be determined by a method relying on fluorescence emission measurement. Such method utilizes a nucleic acid ligand to the target and a ligand beacon comprising: i) a nucleic acid sequence complimentary to at least a portion of said nucleic acid ligand, ii) a fluorescent group, and iii) a fluorescence-modifying group. The emission profile of the ligand beacon is altered based on the presence and/or concentration change of the target in the test mixture.

4 Claims, 8 Drawing Sheets

Quenched Fluorophore

Fluorescence

US 6,177,555 B1

HOMOGENEOUS DETECTION OF A TARGET THROUGH NUCLEIC ACID LIGAND-LIGAND BEACON INTERACTION

RELATED APPLICATIONS

This application is a continuation of U.S. patent application Ser. No. 09/157,206, filed Sep. 18, 1998, U.S. Pat. No. 5,989,823, entitled "Homogeneous Detection of a Target Through Nucleic Acid Ligand-ligand Beacon Interaction."

FIELD OF THE INVENTION

This invention is directed to a novel method for the highly selective detection of specific target molecules. The binding of a nucleic acid ligand to a target molecule is accompanied by a change in the fluorescence spectrum of the assay solution. The subject invention will be useful in any application where it is desired to detect a target molecule.

BACKGROUND OF THE INVENTION

The ability to detect the presence of a specific target molecule, such as a nucleic acid or a protein, has proved to have increasing importance in a large number of applications. One of the most significant applications utilizing sensitive and selective detection of such target molecules is in diagnostic assays. In these assays, measurement of the concentration of a target molecule is used to yield diagnostic or prognostic medical information.

A recently described reagent for nucleic acid detection is the "molecular beacon". A molecular beacon is a unimolecular nucleic acid molecule comprising a stem-loop structure (FIG. 1). The stem is formed by intramolecular base pairing of two complementary sequences such that the 5' and 3' ends of the nucleic acid are at the base of the stem. The loop links the two strands of the stem, and is comprised of sequences complementary to those to be detected. A fluorescent group (star in FIG. 1) is covalently attached to one end of the molecule, and a fluorescent quenching group (filled circle in FIG. 1) is attached to the other end. In the stem-loop configuration, these two moieties are physically adjacent to one another. When the molecular beacon is illuminated with light corresponding to the excitation wavelength of the fluorescent group, no fluorescence is observed. This is because energy transfer occurs between the fluorescent group and the quenching group such that light emitted from the fluorescent group upon excitation is absorbed by the quenching group.

When the molecular beacon is contacted with sequences complementary to the loop, the loop hybridizes to this sequence. This process is energetically favored as the intermolecular duplex formed is longer, and therefore more stable, than the intramolecular duplex formed in the stem region. As this intermolecular double helix forms, torsional forces are generated that cause the stem region to unwind. As a result, the fluorescent group and the quenching group become spatially separated such that the quenching group is no longer able to efficiently absorb light emitted from the fluorescent group. Thus, binding of the molecular beacon to its target nucleic acid sequence is accompanied by an increase in fluorescence emission from the fluorescent group.

It is possible to simultaneously use two or more molecular beacons with different sequence specificities in the same assay. In order to do this, each molecular beacon is labeled with at least a different fluorescent group. The assay is then monitored for the spectral changes characteristic for the binding of each particular molecular beacon to its complementary sequence. In this way, molecular beacons have been used to determine whether an individual is homozygous wild-type, homozygous mutant or heterozygous for a particular mutation. For example, using one quenched-fluorescein molecular beacon that recognizes the wild-type sequence and another rhodamine-quenched molecular beacon that recognizes a mutant allele, it is possible to genotype individuals for the β-chemokine receptor (Kostrikis et al. (1998) Science 279:1228–1229). The presence of only a fluorescein signal indicates that the individual is wild-type, and the presence of rhodamine signal only indicates that the individual is a homozygous mutant. The presence of both rhodamine and fluorescein signal is diagnostic of a heterozygote. Tyagi et al. ((1998) Nature Biotechnology 16: 49–53) have even described the simultaneous use of four differently labeled molecular beacons for allele discrimination.

Although useful for the detection of nucleic acid targets, molecular beacons have not been used for detecting other types of molecules. Indeed, there has been no suggestion made in the extensive art that molecular beacons can be used for anything other than detecting specific nucleic acids in mixtures containing a plurality of nucleic acids. Detection of nucleic acids is undeniably important, but in many applications— especially medical diagnostic scenarios— detection of non-nucleic acid molecules, such as proteins, sugars, and small metabolites, is required.

In general, the detection of non-nucleic acid target molecules is a more complicated matter than the detection of nucleic acids, and no single method is universally applicable. Specific proteins may be detected through the use of antibody-based assays, such as an enzyme linked immunoassay (ELISA). In one form of ELISA, a primary antibody binds to the protein of interest, and signal amplification is achieved by using a labeled secondary antibody that can bind to multiple sites on the primary antibody. This technique can only be used to detect molecules for which specific antibodies exist. The generation of new antibodies is a time consuming and very expensive procedure, and many proteins are not sufficiently immunogenic to generate antibodies in host animals. Furthermore, it is often necessary to measure and detect small molecules, such as hormones and sugars, that are generally not amenable to antibody recognition. In these cases, enzymatic assays for the specific molecule are often required.

The dogma for many years was that nucleic acids had primarily an informational role. Through a method known as Systematic Evolution of Ligands by EXponential enrichment, termed the SELEX™ process, it has become clear that nucleic acids have three dimensional structural diversity similar to or even more than proteins. The SELEX™ process is a method for the in vitro evolution of nucleic acid molecules with highly specific binding to target molecules and is described in U.S. patent application Ser. No. 07/536,428, filed Jun. 11, 1990, entitled "Systematic Evolution of Ligands by Exponential Enrichment," now abandoned; U.S. patent application Ser. No. 07/714,131, filed Jun. 10, 1991, entitled "Nucleic Acid Ligands," now U.S. Pat. No. 5,475,096; U.S. patent application Ser. No. 07/93 1,473, filed Aug. 17, 1992, entitled "Methods for Identifying Nucleic Acid Ligands," now U.S. Pat. No. 5,270,163 (see also, WO 91/19813), each of which is specifically incorporated by reference herein. Each of these applications, collectively referred to herein as the SELEX™ Patent Applications, describes a fundamentally novel method for making a nucleic acid ligand to any desired target molecule. The SELEX™ process provides a class of products which are referred to as nucleic acid ligands, each ligand having a unique sequence, and which has the property of binding specifically to a desired target compound or molecule. Each SELEX™ process-identified nucleic acid ligand is a specific ligand of a given target compound or molecule. The SELEX™ process is based on the unique insight that inucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets.

The SELEX™ method involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX™ method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific high affinity nucleic acid ligands to the target molecule.

It has been recognized that the SELEX™ method demonstrates that nucleic acids as chemical compounds can form a wide array of shapes, sizes and configurations, and are capable of a far broader repertoire of binding and other functions than those displayed by nucleic acids in biological systems.

The basic SELEX™ method has been modified to achieve a number of specific objectives. For example, U.S. patent application Ser. No. 07/960,093, filed Oct. 14, 1992, entitled "Method for Selecting Nucleic Acids on the Basis of Structure," now abandoned in favor of U.S. patent application Ser. No. 08/198,670, filed Feb. 22, 1994, now U.S. Pat. No. 5,707,796, describes the use of the SELEX™ process in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands," now abandoned in favor of U.S. patent application Ser. No. 08/612,895, filed Mar. 8, 1996, abandoned in favor of U.S. patent application Ser. No. 08/443,957, now U.S. Pat. No. 5,763,177, describes a SELEX™ process-based method for selecting nucleic acid ligands containing photoreactive groups capable of binding and/or photocrosslinking to and/or photoinactivating a target molecule. U.S. patent application Ser. No. 08/134,028, filed Oct. 7, 1993, entitled "High-Affinity Nucleic Acid Ligands That Discriminate Between Theophylline and Caffeine," abandonedin favor of U.S. patent application Ser. No. 08/461,069, now U.S. Pat. No. 5,580,737, describes a method for identifying highly specific nucleic acid ligands able to discriminate between closely related molecules, which can be non-peptidic, termed Counter-SELEX™. U.S. patent application Ser. No. 08/143,564, filed Oct. 25, 1993, entitled "Systematic Evolution of Ligands by Exponential Enrichment: Solution SELEX™," now U.S. Pat. No. 5,567,588, describes a SELEX™ process-based method which achieves highly efficient partitioning between oligonucleotides having high and low affinity for a target molecule.

The SELEX™ method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX™ process-identified nucleic acid liganids containing modified nucleotides are described in U.S. patent application Ser. No. 08/117,991, filed Sep. 8, 1993, entitled "High Affinity nucleic acid ligands Containing Modified Nucleotides," abandoned in favor of U.S. patent application Ser. No. 08/430,709, now U.S. Pat. No. 5,660,985, that describes oligonucleotides containing nucleotide derivatives chemically modified at the 5- and 2'-positions of pyrimidines. U.S. patent application Ser. No. 08/134,028, supra, describes highly specific nucleic acid ligands containing one or more nucleotides modified with 2'-amino (2'-$NH_2$), 2'-fluoro (2'-F), and/or 2'-O-methyl (2'-OMe). U.S. patent application Ser. No. 08/264,029, filed Jun. 22, 1994, entitled "Novel Method of Preparation of 2' Modified Pyrimidine Intramolecular Nucleophilic Displacement," now abandoned in favor of U.S. patent application Ser. No. 08/732,283 filed Oct. 30, 1996, U.S. Pat. No. 6,090,932, describes oligonucleotides containing various 2'-modified pyrimidines.

The SELEX™ method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX™," now U.S. Pat. No. 5,637,459, and U.S. patent application Ser. No. 08/234,997, filed Apr. 28, 1994, entitled "Systematic Evolution of Ligands by Exponential Enrichment: Blended SELEX™, "now U.S. Pat. No. 5,683,867, respectively. These applications allow the combination of the broad array of shapes and other properties, and the efficient amplification and replication properties, of oligonucleotides with the desirable properties of other molecules.

The SELEX™ method further encompasses combining selected nucleic acid ligands with lipophilic compounds or non-immunogenic, high molecular weight compounds in a diagnostic or therapeutic complex as described in U.S. patent application Ser. No. 08/434,465, filed May 4, 1995, U.S. Pat. No. 6,011,020, entitled "Nucleic Acid Complexes". VEGF nucleic acid ligands that are associated with a lipophilic compound, such as diacyl glycerol or dialkyl glycerol, in a diagnostic or therapeutic complex are described in U.S. patent application Ser. No. 08/739,109, filed Oct. 25, 1996, entitled "Vascular Endothelial Growth Factor (VEGF) Nucleic Acid Ligand Complexes", now U.S. Pat. No. 5,859,228, VEGF nucleic acid ligands that are associated with a lipophilic compound, such as a glycerol lipid, or a non-immunogenic, high molecular weight compound, such as polyethylene glycol, are further described in U.S. patent application Ser. No. 08/897,351, filed Jul. 21, 1997, U.S. Pat. No. 6,051,698 entitled "Vascular Endothelial Growth Factor (VEGF) Nucleic Acid Ligand Complexes." VEGF nucleic acid ligands that are associated with a non-immunogenic, high molecular weight compound or lipophilic compound are also further described in PCT/US97/18944, filed Oct. 17, 1997, entitled "Vascular Endothelial Growth Factor (VEGF) Nucleic Acid Ligand Complexes." Each of the above described patent applications which describe modifications of the basic SELEX™ procedure are specifically incorporated by reference herein in their entirety.

It is an object of the present invention to provide methods that can be used to detect virtually any non-nucleic acid target molecule in a test mixture, using nucleic acid reagents that are easily and cheaply manufactured.

It is a further object of the instant invention to provide a method for adapting molecular beacons in order to detect non-nucleic acid target molecules in a test mixture.

Another object of the instant invention is to provide a single, universal assay for virtually any non-nucleic acid target molecule in which measurements of fluorescence emission are used to determine the concentration of the target.

SUMMARY OF THE INVENTION

The present invention includes methods for detecting the binding of nucleic acid ligands to their cognate target molecules. The methods rely on the insight that nucleic acid ligands can be recognized by molecular beacons in a target-dependent context. The methods and reagents described herein allow, for the first time, virtually any target molecule to be detected through simple fluorescence emission measurements.

The invention uses novel molecular beacons, termed ligand beacons, that hybridize to nucleic acid ligands only under preselected conditions. In some embodiments, the ligand beacon can only hybridize to nucleic acid ligands that are free of their cognate target; in other embodiments, the ligand beacon can only hybridize to nucleic acid ligands that are bound to their cognate targets. In either case, the binding of nucleic acid ligand to target is accompanied by a measurable change in the spectral properties of the ligand beacon. Conventional molecular beacons known in the art are used to recognize complementary nucleic acid sequences, e.g., genomic sequences and sequences specific to pathogens. By contrast, ligand beacons recognize nucleic acid ligands with both a particular sequence and a particular configuration. The configuration of the nucleic acid ligand changes when it is or is not bound to its cognate target.

The methods described herein provide, for the first time, a single universal method for target molecule detection which simply involves analyzing fluorescence emission. The reagents and methods described herein are particularly suitable for diagnostic assays. Diagnostic assays that require quantitative measurements (e.g., measurements of a hormone or sugar level) are possible according to the present invention by simply comparing the fluorescence measurement with that obtained from a control. Similarly, diagnostic assays requiring qualitative detection of substances (e.g., presence of a mutated gene product, or presence of a pathogen) are also possible. The reagents can be used in assays for single substances, or they can be used to simultaneously monitor a variety of substances in a single assay. Using different fluorescent groups with spectroscopically resolvable emission spectra, this method allows for the simultaneous detection of multiple targets in a single vessel. In this homogeneous multiplexing approach, distinct fluorescent groups can be attached to different nucleic acid ligands specific to targets of interest. In particular, the invention provide methods for performing assays using reagents attached to solid supports. In these embodiments, a plurality of nucleic acid ligands are attached to spatially discrete regions on solid supports, and contacted with the solution to be assayed. Using the detection methods described herein, measurements of fluorescence at discrete sites on the solid support can reveal whether particular substances are present in the assay solution, and in what quantities. In this way, it is possible to assay for a plurality—potentially hundreds or even thousands—of different substances in a single test. Arrays of nucleic acid ligands that can be used with the methods and reagents described herein are detailed in co-pending and commonly-assigned U.S. patent application Ser. No. 08/990,436, filed Dec. 15, 1997, entitled "Nucleic Acid Ligand Diagnostic Biochip" which is incorporated herein by reference in its entirety.

DETAILED DESCRIPTION OF THE INVENTION

Figure 1:
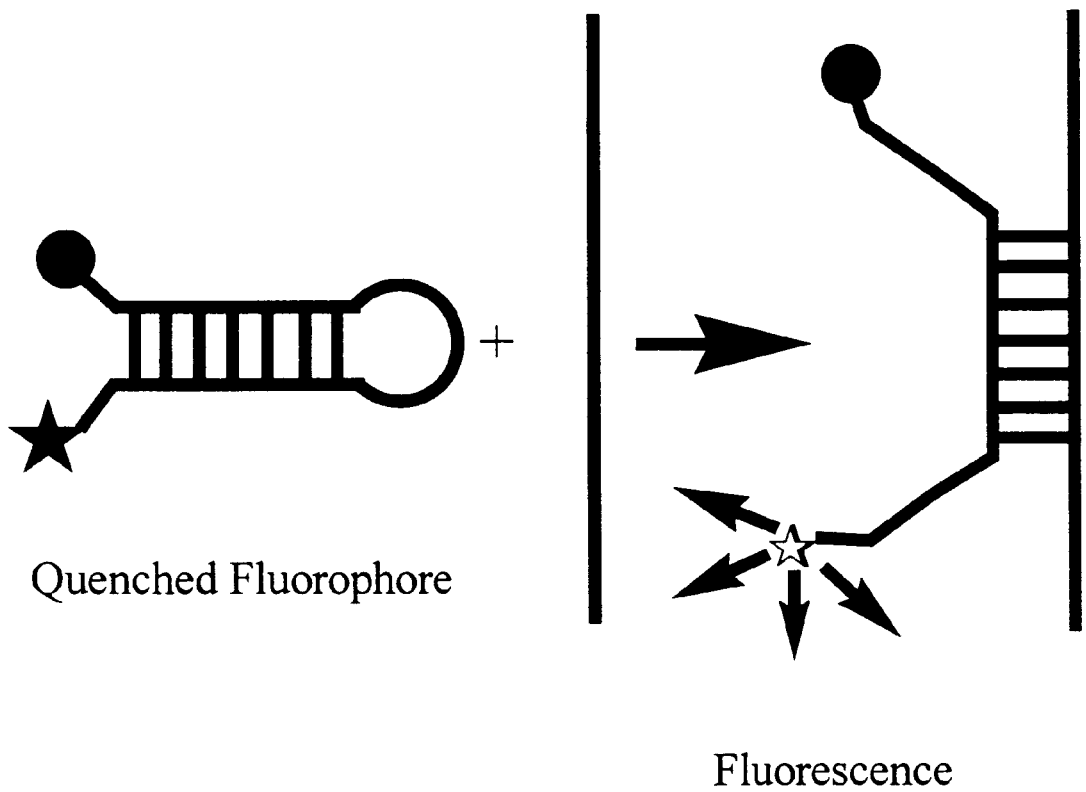
FIG. 1 depicts the use of molecular beacons, wherein the star represents a fluorescent group and the filled circle represents a quenching group.

The SELEX™ method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX™ process-identified nucleic acid ligands containing modified nucleotides are described in U.S. patent application Ser. No. 08/117,991, filed Sep. 8, 1993, entitled "High Affinity Nucleic Acid Ligands Containing Modified Nucleotides", abandoned in favor of U.S. patent application Ser. No. 08/430,709, filed Apr. 27, 1995, now U.S. Pat. No. 5,660,985, that describes oligonucleotides containing nucleotide derivatives chemically modified at the 5- and 2'-positions of pyrimidines. U.S. patent application Ser. No. 08/134,028, above, describes highly specific nucleic acid ligands containing one or more nucleotides modified with 2'-amino (2'-NH$_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2' Modified Nucleosides by Intramolecular Nucleophilic Displacement", now abandoned in favor of U.S. patent application Ser. No. 08/732,283, filed Oct. 30, 1996, describes oligonucleotides containing various 2'-modified pyrimidines.

The methods of the instant invention have the ability to detect virtually any target molecule of interest through the production of a highly specific spectral shift. Importantly, as the target molecule probes are nucleic acids, they are particularly useful in "biochip" applications well known in the art. This art provides many efficient methods for coupling nucleic acids to the surface of solid supports in spatially specific ways. The methods and embodiments disclosed herein will therefore be useful in biochip-based medical screening applications as described in the co-pending and commonly assigned U.S. patent application Ser. No. 08/990,436, filed Dec. 15, 1997, entitled "Nucleic Acid Ligand Diagnostic Biochip", and specifically incorporated herein by reference. In addition, the methods of the invention will be useful in the diagnosis of blood clotting disorders as described in co-pending and commonly assigned U.S. patent application Ser. No. 09/159,338, filed Sep. 18, 1998, entitled "Factor V Leiden Detection".

Definitions

Various terms are used herein to refer to aspects of the present invention. To aid in the clarification of the description of the components of this invention, the following definitions are provided:

As used herein, "nucleic acid ligand" refers to a non-naturally occurring nucleic acid having a desirable action on a target. A desirable action includes, but is not limited to, binding of the target, catalytically changing the target, reacting with the target in a way which modifies/alters the target or the functional activity of the target, covalently attaching to the target as in a suicide inhibitor, facilitating the reaction between the target and another molecule. In the preferred embodiment, the action is specific binding affinity for a target molecule, such target molecule being a three dimensional chemical structure other than a polynucleotide that binds to the nucleic acid ligand through a mechanism which predominantly depends on Watson/Crick base pairing or triple helix binding, wherein the nucleic acid ligand is not a nucleic acid having the known physiological function of being bound by the target molecule. Nucleic acid ligands include nucleic acids that are identified from a candidate mixture of nucleic acids, said nucleic acid ligand being a ligand of a given target, by the method comprising: a) contacting the candidate mixture with the target, wherein nucleic acids having an increased affinity to the target relative to the candidate mixture may be partitioned from the remainder of the candidate mixture; b) partitioning the increased affinity nucleic acids from the remainder of the candidate mixture; and c) amplifying the increased affinity nucleic acids to yield a ligand-enriched mixture of nucleic acids.

As used herein, "candidate mixture" refers to a mixture of nucleic acids of differing sequence from which to select a desired ligand. The source of a candidate mixture can be from naturally-occurring nucleic acids or fragments thereof, chemically synthesized nucleic acids, enzymatically synthesized nucleic acids or nucleic acids made by a combination of the foregoing techniques. In a preferred embodiment, each nucleic acid has fixed sequences surrounding a randomized region to facilitate the amplification process.

As used herein, "nucleic acid" means either DNA, RNA, single-stranded or double-stranded, and any chemical modifications thereof. Modifications include, but are not limited to, those which provide other chemical groups that incorporate additional charge, polarizability, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases isocytidine and isoguanidine and the like. Modifications can also include 3' and 5' modifications such as capping.

As used herein, "SELEX™" methodology involves the combination of selection of nucleic acid ligands which interact with a target in a desirable manner, for example binding to a protein, with amplification of those selected nucleic acids. Optional iterative cycling of the selection/amplification steps allows selection of one or a small number of nucleic acids which interact most strongly with the target from a pool which contains a very large number of nucleic acids. Cycling of the selection/amplification procedure is continued until a selected goal is achieved. The SELEX™ methodology is described in the SELEX™ Patent Applications.

As used herein "target" means any compound or molecule of interest for which a diagnostic test is desired and where a nucleic acid ligand is known or can be identified. A target can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, etc. without limitation.

As used herein, "solid support" means any microfabricated solid surface to which molecules may be attached through either covalent or non-covalent bonds. This includes, but is not limited to, Langmuir-Bodgett films, functionalized glass, membranes, charged paper, nylon, germanium, silicon, PTFE, polystyrene, gallium arsenide, gold, and silver. Any other material known in the art that is capable of having functional groups such as amino, carboxyl, thiol or hydroxyl incorporated on its surface, is contemplated. This includes surfaces with any topology, such spherical surfaces and grooved surfaces.

As used herein, "bodily fluid" refers to a mixture of molecules obtained from an organism. This includes, but is not limited to, whole blood, blood plasma, urine, semen, saliva, lymph fluid, meningal fluid, amniotic fluid, glandular fluid, sputum, and cerebrospinal fluid. This also includes experimentally separated fractions of all of the preceding. Bodily fluid also includes solutions or mixtures containing homogenized solid material, such as feces, tissues, and biopsy samples.

As used herein, "test mixture" refers to any sample that contains a plurality of molecules. This includes, but is not limited to, bodily fluids as defined above, and any sample for environmental and toxicology testing such as contaminated water and industrial effluent.

As used herein, "fluorescent group" refers to a molecule that, when excited with light having a selected wavelength, emits light of a different wavelength. Fluorescent groups include, but are not limited to, fluorescein, tetramethylrhodamine, Texas Red, BODIPY, 5-[(2-aminoethyl)amino]napthalene-1-sulfonic acid (EDANS), and Lucifer yellow. Fluorescent groups may also be referred to as "fluorophores".

As used herein, "fluorescence-modifying group" refers to a molecule that can alter in any way the fluorescence emission from a fluorescent group. A fluorescence-modifying group generally accomplishes this through an energy transfer mechanism. Depending on the identity of the fluorescence-modifying group, the fluorescence emission can undergo a number of alterations, including, but not limited to, attenuation, complete quenching, enhancement, a shift in wavelength, a shift in polarity, a change in fluorescence lifetime. One example of a fluorescence-modifying group is a quenching group.

As used herein, "energy transfer" refers to the process by which the fluorescence emission of a fluorescent group is altered by a fluorescence-modifying group. If the fluorescence-modifying group is a quenching group, then the fluorescence emission from the fluorescent group is attenuated (quenched). Energy transfer can occur through fluorescence resonance energy transfer, or through direct energy transfer. The exact energy transfer mechanisms in these two cases are different. It is to be understood that any reference to energy transfer in the instant application encompasses all of these mechanistically-distinct phenomena.

As used herein, "energy transfer pair" refers to any two molecules that participate in energy transfer. Typically, one of the molecules acts as a fluorescent group, and the other acts as a fluorescence-modifying group. The preferred energy transfer pair of the instant invention comprises a fluorescent group and a quenching group. In some cases, the distinction between the fluorescent group and the fluorescence-modifying group may be blurred. For example, under certain circumstances, two adjacent fluorescein groups can quench one another's fluorescence emission via direct energy transfer. For this reason, there is no limitation on the identity of the individual members of the energy transfer pair in this application. All that is required is that the spectroscopic properties of the energy transfer pair as a whole change in some measurable way if the distance between the individual members is altered by some critical amount.

"Energy transfer pair" is used to refer to a group of molecules that form a single complex within which energy transfer occurs. Such complexes may comprise, for example, two fluorescent groups which may be different from one another and one quenching group, two quenching groups and one fluorescent group, or multiple fluorescent groups and multiple quenching groups. In cases where there are multiple fluorescent groups and/or multiple quenching groups, the individual groups may be different from one another e.g., one complex contemplated herein comprises fluorescein and EDANS as fluorescent groups, and DABCYL as a quenching agent.

As used herein, "quenching group" refers to any fluorescence-modifying group that can attenuate at least partly the light emitted by a fluorescent group. We refer herein to this attenuation as "quenching". Hence, illumination of the fluorescent group in the presence of the quenching group leads to an emission signal that is less intense than expected, or even completely absent. Quenching occurs through energy transfer between the fluorescent group and the quenching group. The preferred quenching group of the invention is (4-dimethylamino-phenylazo)benzoic acid (DABCYL).

As used herein, "fluorescence resonance energy transfer" or "FRET" refers to an energy transfer phenomenon in which the light emitted by the excited fluorescent group is absorbed at least partially by a fluorescence-modifying group. If the fluorescence-modifying group is a quenching group, then that group can either radiate the absorbed light as light of a different wavelength, or it can dissipate it as heat. FRET depends on an overlap between the emission spectrum of the fluorescent group and the absorption spectrum of the quenching group. FRET also depends on the distance between the quenching group and the fluorescent group. Above a certain critical distance, the quenching group is unable to absorb the light emitted by the fluorescent group, or can do so only poorly.

As used herein "direct energy transfer" refers to an energy transfer mechanism in which passage of a photon between the fluorescent group and the fluorescence-modifying group does not occur. Without being bound by a single mechanism, it is believed that in direct energy transfer, the fluorescent group and the fluorescence-modifying group interfere with each others electronic structure. If the fluorescence-modifying group is a quenching group, this will result in the quenching group preventing the fluorescent group from even emitting light. Quenching groups and fluorescent groups are frequently close enough together in the stern of ligand beacons that direct energy transfer can take place. For example, when DABCYL is located on one terminus of a ligand beacon, this quenching group can efficiently quench almost all fluorescent groups on the other terminus through direct energy transfer.

In general, quenching by direct energy transfer is more efficient than quenching by FRET. Indeed, some quenching groups that do not quench particular fluorescent groups by FRET (because they do not have the necessary spectral overlap with the fluorescent group) can do so efficiently by direct energy transfer. Furthermore, some fluorescent groups can act as quenching groups themselves if they are close enough to other fluorescent groups to cause direct energy transfer. For example, under these conditions, two adjacent fluorescein groups can quench one another's fluorescence effectively. For these reasons, there is no limitation on the nature of the fluorescent groups and quenching groups useful for the practice of this invention.

As used herein, "ligand beacon" refers to a nucleic acid molecule, labeled with an energy transfer pair, that can specifically hybridize to a nucleic acid ligand under preselected conditions. Upon doing so, the ligand beacon undergoes a conformational change that causes the members of the energy transfer pair to move relative to one another such that the emission from the fluorescent group is modified. Preferred energy transfer pairs comprise a fluorescent group and a quenching group. In preferred embodiments, the ligand beacon comprises a unimolecular stem-loop nucleic acid, wherein the fluorescent group and the quenching group are at the termini of the nucleic acid, and the loop comprises sequences that are at least partially complementary to sequences within the nucleic acid ligand. In some embodiments, the ligand beacon can only hybridize to the nucleic acid ligand when the nucleic acid ligand is not bound to its target. In other embodiments, the ligand beacon can only hybridize when the nucleic acid ligand is bound to its cognate target. In either case, hybridization of the ligand beacon to the nucleic acid ligand is accompanied by a change in the fluorescence emission intensity of the ligand beacon.

Although the ligand beacon comprises a unimolecular stem-loop nucleic acid in preferred embodiments, there is no limitation on the structure of the ligand beacon. Any nucleic acid that can hybridize to a nucleic acid ligand, and in doing so undergo a conformational change that alters the distance between nucleotides, is contemplated in the instant invention. For example, nucleic acid configured as G-quartets may be useful in this invention. These nucleic acid structures are formed by hydrogen bonding between the Hoogsteen and Watson-Crick faces of four spatially adjacent guanosines. Adjacent quartets can stack on top of one another to form a highly symmetric and regular complex. Similarly, ligand beacons that undergo conformational changes in which initially separated nucleotide positions become adjacent upon hybridizing to nucleic acid ligands are also included in the invention. These latter ligand beacons, when labeled with fluorescent groups and quenching groups at the appropriate nucleotide positions, undergo a decrease in fluorescence intensity upon binding to the nucleic acid ligand.

In the preferred embodiment, the nucleic acid ligands of the present invention are derived from the SELEX™ methodology. The SELEX™ process is described in U.S. patent application Ser. No. 07/536,428, entitled "Systematic Evolution of Ligands by EXponential Enrichment," now abandoned, U.S. patent application Ser. No. 07/714,131, filed Jun. 10, 1991, entitled "Nucleic Acid Ligands," now U.S. Pat. No. 5,475,096, U.S. patent application Ser. No. 07/931,473, filed Aug. 17, 1992, entitled "Methods for Identifying Nucleic Acid Ligands", now U.S. Pat. No. 5,270,163 (see also, WO 91/19813). These applications, each specifically incorporated herein by reference, are collectively called the SELEX™ Patent Applications.

The SELEX™ process provides a class of products which are nucleic acid molecules, each having a unique sequence, and each of which has the property of binding specifically to a desired target compound or molecule. Target molecules are preferably proteins, but can also include among others carbohydrates, peptidoglycans and a variety of small molecules. SELEX™ methodology can also be used to target biological structures, such as cell surfaces or viruses, through specific interaction with a molecule that is an integral part of that biological structure.

In its most basic form, the SELEX™ process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity for the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX™ process will yield a candidate mixture containing one or a small number of unique nucleic acids representing those nucleic acids from the original candidate mixture having the highest affinity to the target molecule.

The basic SELEX™ method has been modified to achieve a number of specific objectives. For example, U.S. patent application Ser. No. 07/960,093, filed Oct. 14, 1992, entitled "Method for Selecting Nucleic Acids on the Basis of Structure," now abandoned in favor of U.S. patent application Ser. No. 08/198,670, filed Feb. 22, 1994, now U.S. Pat. No. 5,707,796, describes the use of the SELEX™ process in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands," now abandoned in favor of U.S. patent application Ser. No. 08/612,895, filed Mar. 8, 1996, now U.S. Pat. No. 5,763,177, describes a SELEX™ based method for selecting nucleic acid ligands containing photoreactive groups capable of binding and/or photocrosslinking to and/or photoinactivating a target molecule. U.S. patent application Ser. No. 08/134,028, filed Oct. 7, 1993, entitled "High-Affinity Nucleic Acid Ligands That Discriminate Between Theophylline and Caffeine," now U.S. Pat. No. 5,580,737, describes a method for identifying highly specific nucleic acid ligands able to discriminate between closely related molecules, termed Counter-SELEX™. U.S. patent application Ser. No. 08/143,564, filed Oct. 25, 1993, entitled "Systematic Evolution of Ligands by Exponential Enrichment: Solution SELEX™," abandoned in favor of U.S. patent application Ser. No. 08/461,069, now U.S. Pat. No. 5,567,588, describes a SELEX™-based method which achieves highly efficient partitioning between oligonucleotides having high and low affinity for a target molecule. U.S. patent application Ser. No. 07/964,624, filed Oct. 21, 1992, entitled "Nucleic Acid Ligands to HIV-RT and HIV-1 Rev," now U.S. Pat. No. 5,496,938, describes methods for obtaining improved nucleic acid ligands after SELEX™ has been performed. U.S. patent application Ser. No. 08/400,440, filed Mar. 8, 1995, entitled "Systematic Evolution of Ligands by Exponential Enrichment: Chemi-SELEX™," now U.S. Pat. No. 5,705,337, describes methods for covalently linking a ligand to its target.

The SELEX™ method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX™ process-identified nucleic acid ligands containing modified nucleotides are described in U.S. patent application Ser. No. 08/117,991, filed Sep. 8, 1993, entitled "High Affinity Nucleic Acid Ligands Containing Modified Nucleotides," now U.S. Pat. No. 5,660,985, that describes oligonucleotides containing nucleotide derivatives chemically modified at the 5- and 2'-positions of pyrimidines. U.S. patent application Ser. No. 08/134,028, supra, describes highly specific nucleic acid ligands containing one or more nucleotides modified with 2'-amino (2'-NH$_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2' Modified Nucleosides by Intramolecular Nucleophilic Displacement," abandoned in favor of U.S. patent application Ser. No. 08/732,283, filed Oct. 30, 1996, describes oligonucleotides containing various 2'-modified pyrimidines.

The SELEX™ method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX™," now U.S. Pat. No. 5,637,459, and U.S. patent application Ser. No. 08/234,997, filed Apr. 28, 1994, entitled "Systematic Evolution of Ligands by Exponential Enrichment: Blended SELEX™," abandoned in favor of U.S. patent application Ser. No. 5,683,867, respectively. These applications allow the combination of the broad array of shapes and other properties, and the efficient amplification and replication properties, of oligonucleotides with the desirable properties of other molecules.

The SELEX™ process provides high affinity ligands of a target molecule. This represents a singular achievement that is unprecedented in the field of nucleic acids research.

In co-pending and commonly assigned U.S. patent application Ser. No. 07/964,624, filed Oct. 21, 1992, methods are described for obtaining improved nucleic acid ligands after the SELEX™ process has been performed (now U.S. Pat. No. 5,496,938). This patent, entitled "Nucleic Acid Ligands to HIV-RT and HIV-1 Rev," along with each of the patent applications discussed above, is specifically incorporated herein by reference.

One potential problem encountered in the diagnostic use of nucleic acids is that oligonucleotides in their phosphodiester form may be quickly degraded in bodily fluids by intracellular and extracellular enzymes such as endonucleases and exonucleases before the desired effect is manifest. Certain chemical modifications of the nucleic acid ligand can be made to increase the in vivo stability of the nucleic acid ligand or to enhance or to mediate the delivery of the nucleic acid ligand. See, e.g., U.S. patent application Ser. No. 08/117,991, filed Sep. 8, 1993, entitled "High Affinity Nucleic Acid Ligands Containing Modified Nucleotides," abandoned in favor of U.S. patent application Ser. No. 08/430,709, now U.S. Pat. No. 5,660,985, which is specifically incorporated herein by reference. Modifications of the nucleic acid ligands contemplated in this invention include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, unusual base-pairing combinations such as the isobases isocytidine and isoguanidine and the like. Modifications can also include 3' and 5' modifications such as capping.

The modifications can be pre- or post-SELEX™ process modifications. Pre-SELEX™ process modifications yield nucleic acid ligands with both specificity for their SELEX™ target and improved in vivo stability. Post-SELEX™ process modifications made to 2'-OH nucleic acid ligands can result in improved in vivo stability without adversely affecting the binding capacity of the nucleic acid ligand.

Other modifications are known to one of ordinary skill in the art. Such modifications may be made post-SELEX™ process (modification of previously identified unmodified ligands) or by incorporation into the SELEX™ process.

Ligand beacons

In one embodiment of the invention, a ligand beacon is used to detect a nucleic acid ligand that is or is not bound to its cognate target. The ligand beacon preferably consists of a single-stranded DNA molecule that assumes a stem-loop structure in solution. In this embodiment, the stem of the ligand beacon is formed by the intramolecular base-pairing of two antiparallel strands of nucleic acid. The 5' terminus of one strand is linked to the 3' terminus of the other strand with a loop of single stranded DNA. These nucleic acid molecules can be rapidly synthesized as single-stranded oligonucleotides with the general structure:

wherein sequence A' is both complementary in sequence and reversed in orientation relative to A. When heat-denatured and slowly cooled, this oligonucleotide will form a stem-loop structure wherein the dashed line forms the loop, and wherein A and A' pair to form the stem.

Figure 2:
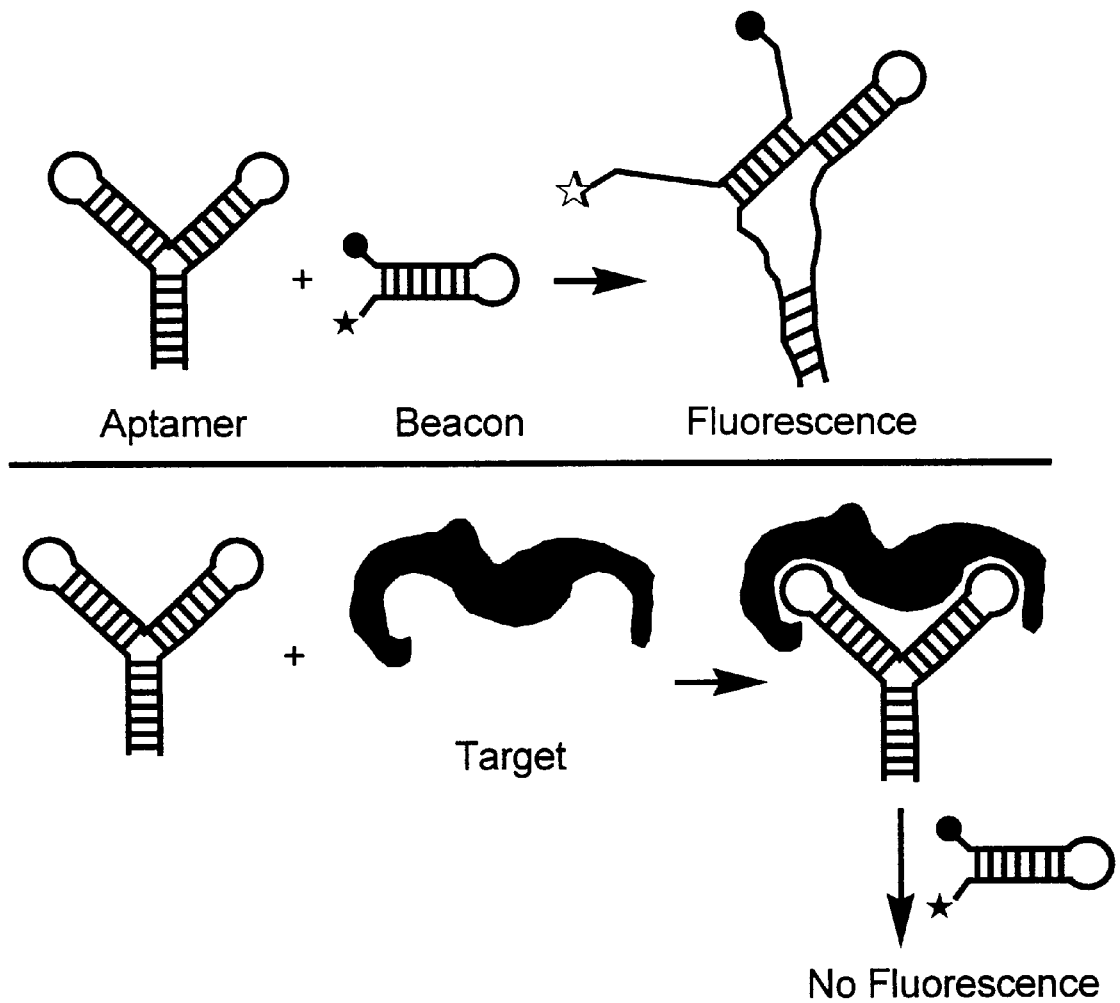
FIG. 2 depicts the use of ligand beacons. This ligand beacon can only hybridize to a nucleic acid ligand that is free of its cognate target. Upon hybridization, fluorescence is generated as the fluorescent group (star) is separated from the quenching group (filled circle).

The loop domain comprises sequences that are at least partially complementary to a region of the nucleic acid ligand. In preferred embodiments, the sequences are chosen such that they can only hybridize to one another when the nucleic acid ligand is not bound to its cognate target (FIG. 2). Furthermore, when the ligand beacon hybridizes to the nucleic acid ligand, the nucleic acid ligand can no longer bind to its cognate target. In particularly preferred embodiments, the loop of the ligand beacon binds to a sequence in the nucleic acid ligand that is at least about 20 nucleotides long; the stem region of the ligand beacon is preferably shorter.

The formation of the intermolecular duplex between the loop of the ligand beacon and the target-free nucleic acid ligand is energetically favored because the resulting duplex is longer, and hence more stable, than the intramolecular duplex. As the loop sequence and the nucleic acid ligand form a duplex, torsional forces are developed in the ligand beacon. These forces are transmitted to the stem region which unwinds in response, usually starting at the base of the stem where the termini are located. One base pair in the stem is unwound for each new base pair that is made between the ligand beacon and the nucleic acid ligand. Thus nucleotide positions that were adjacent to one another on opposite sides of the stem become separated. In particular, because unwinding begins at the base of the stem, the termini of the ligand beacon become widely separated (FIG. 2).

In some embodiments, nucleotide positions in the ligand beacon that become separated from one another are labeled with an energy transfer pair. The preferred energy transfer pair of the instant invention comprises a quenching group and a fluorescent group. In preferred embodiments, the nucleotide positions on the ligand beacon that are labeled with the quenching group and the fluorescent group are chosen from those that form the intramolecular stem. In especially preferred embodiments, the 5' and 3' termini of the ligand beacon are labeled with these groups, as the termini become widely separated upon hybridization to the nucleic acid ligand (FIG. 2).

The fluorescent group and the adjacent quenching group take part in energy transfer. In some instances, the energy transfer occurs through fluorescence resonance energy transfer (FRET). FRET takes place when fluorescence emission from a fluorescent group is transferred to an adjacent group that somehow modifies the signal (in this case, quenching the signal). This effect is strongly dependent on the distance between the two groups, such that when separated by a critical distance, FRET does not take place, and the fluorescence emission is unmodified. FRET also requires that the emission spectrum of the fluorescent group overlaps with the absorbance spectrum of the modifying group.

In the instant invention, the preferred fluorescent groups are fluorescein, tetramethylrhodamine, and 5-[(2-aminoethyl)amino]napthalene-1-sulfonic acid (EDANS). The preferred quencher is (4-dimethylaminophenylazo) benzoic acid (DABCYL). When DABCYL and fluorescein or EDANS are close enough together for FRET to occur, DABCYL absorbs light emitted from the fluorescein or EDANS, and dissipates the absorbed energy as heat. As mentioned above, this effect is strongly dependent on the distance between the group. For example, at separations greater than 60 Angstroms, DABCYL is unable to quench the fluorescence from EDANS. DABCYL itself is non-fluorescent at the wavelengths used to excite EDANS or fluorescein.

In other embodiments, the fluorescent group and the quenching group take place in a form of energy transfer termed direct energy transfer. Direct energy transfer occurs when the fluorescent group and the quenching group directly perturb each others electronic structure. When a direct transfer takes place, it is possible for a quenching group to quench at a much higher efficiency and over a broader spectrum than in FRET. Indeed, it has been reported that paired-groups that do not even display FRET, such as Texas Red and DABCYL, can be made to undergo direct energy transfer, leading to the efficient quenching of the fluorescence group by the other group. For example, it has been reported that under such circumstances, the quenching group DABCYL can quench almost all fluorophores (with emission spectra ranging from 475 nm–615 nm) with close to 100% efficiency (Tyagi, et al. 1998. Nature Biotechnology 16: 49–53).

In one preferred embodiment, fluorescein and DABCYL function as a direct energy transfer pair when present at the 5' and 3' termini, even though they are not an efficient FRET Pair. In other embodiments, nucleotide positions that form an individual base pair in the stem are labeled with the fluorescent group and the quenching group. Labeling at these positions also allows direct energy transfer to take place. It is even possible to get fluorescence quenching when two identical fluorescent groups, such as two fluorescein groups, are sufficiently close together.

There is no limitation in the present invention as to the nature of the energy transfer pair, and there is no limitation as to the exact mechanism by which they function together. All that is required is that the spectral properties of the energy transfer pair change in some measurable way as the distance between the individual members of the energy transfer pair is varied.

It is possible to label the ligand beacon with more than one of each member of an energy transfer pair. For example, in some embodiments, two or more nucleotides are labeled with fluorescent groups and the same number of nucleotides are labeled with quenching groups. In preferred embodiments, all of the fluorescent groups are attached to the nucleotides that comprise one strand of the stem, and all of the quenching groups are attached to the nucleotides that comprises the other strand. In these embodiments, more than one base pair in the stem is labeled with both a fluorescent group and a quenching group. Such ligand beacons may give an increased signal relative to singly-labeled ligand beacons upon unwinding of the stem.

Where more than one fluorescent group or more than one quenching group is used, it is not required that there be an equal number of the two groups. For example, the ligand beacon can be labeled with one fluorescent group and two quenching groups. If the sites of labeling are sufficiently close to one another, then more efficient quenching of the fluorescent group would be expected to result. Alternatively, if a given quenching group is capable of quenching more than one fluorescent group, then the separation of a single effective quenching group from multiple fluorescent groups would be expected to give an increased signal relative to separation from a single fluorescent group.

Labeling the ligand beacons with energy transfer pairs can be accomplished easily by standard methods well known in the art. For example, it is possible to incorporate the fluorescent group fluorescein into the ligand beacon at the 5' end during automated oligonucleotide synthesis of the sequence. The quenching group DABCYL can be attached to the ligand beacon by first incorporating an amino group at the 3' end during oligonucleotide synthesis, and then reacting the amino group after synthesis with the succinimidyl ester of DABCYL in anhydrous N,N, dimethyl formamide. Alternatively, DABCYL can be incorporated directly into the ligand beacon during oligonucleotide synthesis. It is important to note that these methods can be adapted to place the members of the energy transfer pair at any location desired in the ligand beacon. In some embodiments it may not be useful to have the labels at the termini. In some instances, for example, it may be preferable to label the stem of the ligand beacon at positions other than the 5' and 3' termini. This is because under certain conditions, the termini of the ligand beacon may temporarily unwind in the absence of free nucleic acid ligand; which can lead to background fluorescence.

It is possible to use fluorescent groups with molecules other than quenching groups. For example, a fluorescent group can be placed next to a modifying group that shifts the emission wavelength, polarizes the emission, or even enhances it. All of these effects result from FRET.

Using the instant methods, it is possible to simultaneously detect multiple target molecules in a test solution using ligand beacons. In this method, each target molecule is recognized by a distinct nucleic acid ligand and each nucleic acid ligand can hybridize to a different ligand beacon. Each ligand beacon in the assay has at least a different loop sequence, specific for a particular nucleic acid ligand, however, it is not necessary that each ligand beacon has a different stem sequence: the stem sequence does not impart the specificity of the ligand beacon, so it is possible to use a common stem for every ligand beacon. In addition, each ligand beacon is labeled with at least a different fluorescent group. For example, to detect two different targets, two different nucleic acid ligands and two different ligand beacons are required. For example, one ligand beacon may be labeled with fluorescein and DABCYL, and the second labeled with rhodamine and DABCYL. Therefore, the concentration of the two targets can be determined in the test solution by monitoring the increase in both fluorescein and rhodamine emission.

It is important to note that it is not necessary to have any structural information about a nucleic acid ligand when designing its cognate ligand beacon. Given the rapidity with which one can synthesize the ligand beacons, only simple, routine experimentation is required to design several different ligand beacons for each nucleic acid ligand, each ligand beacon recognizing a sequence that it at least partially unique. The candidate ligand beacons can be quickly tested to determine which one has the desired activity.

As described above, preferred embodiments use ligand beacons that can bind to nucleic acid ligands only when the nucleic acid ligand is not bound to its target. However, the invention also includes ligand beacons that function in the converse manner. Specifically, the invention also includes ligand beacons that can only hybridize to nucleic acid ligands that are bound to their cognate targets. For example, it is possible to obtain nucleic acid ligands that adopt a primary conformation in the absence of target, but undergo a conformational change upon target binding. Such a conformational change may cause regions of the nucleic acid ligand that are initially double-stranded to become single-stranded. The ligand beacon can hybridize to these single-stranded regions, but not when they are double-stranded. As a result, the increase in fluorescence intensity that occurs upon mixing the nucleic acid ligand, the ligand beacon and the target is directly proportional to the amount of the target.

In other embodiments, the ligand beacon has a structure in which nucleotide positions that are initially separated become adjacent upon hybridizing to the nucleic acid ligand. If these nucleotide positions are labeled as described above with a fluorescent group and a quenching group, then hybridization to the nucleic acid ligand results in a decrease in the ligand beacon's fluorescence emission.

Although the preferred ligand beacons of the invention have a stem-loop architecture, there is no limitation on the structure of ligand beacons. Any nucleic acid structure that undergoes a change in configuration upon hybridizing to a nucleic acid ligand wherein individual nucleotides move relative to one another in a reproducible manner is contemplated herein. It is possible to stack more than one G-quartet on top of each other under appropriate ionic conditions. In this embodiment of the invention, the nucleotides that are located between the G-quartet residues comprise the nucleic acid sequences complementary to the nucleic acid ligand. The G-quartet residues are labeled with the energy transfer pair(s); upon hybridization of the ligand beacon to the nucleic acid ligand, the G-quartet is disrupted, and the energy transfer pair(s) are separated.

In order to determine the concentration of a target molecule in a test mixture, it is preferable to first obtain reference data in which constant amounts of ligand beacon and nucleic acid ligand are contacted with varying amounts of target. The fluorescence emission of each of the reference mixtures is used to derive a graph or table in which target concentration is compared to fluorescence emission. For example, a ligand beacon that a) hybridizes to a target-free nucleic acid ligand; and b) has a stem-loop architecture with the 5' and 3' termini being the sites of fluorescent group and quenching group labeling, could be used to obtain such reference data. Such a ligand beacon would give a characteristic emission profile in which the fluorescence emission decreases as the target concentration increases in the presence of a constant amount of ligand beacon and nucleic acid ligand. Then, a test mixture with an unknown amount of target would be contacted with the same amount of first nucleic acid ligand and second ligand beacon, and the fluorescence emission would be determined. The value of the fluorescence emission would then be compared with the reference data to obtain the concentration of the target in the test mixture.

In some embodiments, the nucleic acid ligand becomes covalently attached to its target molecule in the assay. Methods for obtaining nucleic acid ligands with this capability are described in U.S. patent application Ser. No. 08/123,935, filed Sep. 17, 1993, entitled "Photoselection of Nucleic Acid Ligands", now abandoned, and in U.S. patent application Ser. No. 08/612,895 filed Mar. 8 1996, now U.S. Pat. No. 5,763,177, both of which are specifically incorporated herein in their entirety.

The assays that are possible using ligand beacons are far simpler than conventional techniques for detecting non-nucleic acid target molecules. The assays require only three manipulations: a) addition of the nucleic acid ligand(s); b) addition of the ligand beacons; and c) measurement of the fluorescence. In many embodiments, there is no need to perform any washing steps to remove background signal, unlike the ELISA assays known in the art. Therefore, the present invention provides a single common method that can be applied to virtually any target molecule. Because of the simplicity of the assay, it is particularly well suited to high-throughout automated analysis for medical diagnostic purposes.

In some embodiments, the ligand beacons are used in assays in which nucleic acid ligands are attached to the surface of a solid support. Methods for attaching nucleic acids to solid supports are well known in the art. In these assays, the fluorescence emission from the solid support is monitored after the solid support is contacted with the test mixture suspected of containing the target, and the ligand beacon. It is also possible to use multiple ligand beacons in assays in which a plurality of different nucleic acid ligands are attached to spatially discrete addresses on a solid support, forming an array. Nucleic acid ligand arrays are described in co-pending and commonly assigned U.S. patent application Ser. No. 08/990,436, filed Dec. 15, 1997 entitled "Nucleic Acid Ligand Diagnostic Biochip", specifically incorporated herein by reference in its entirety. These assays require that each nucleic acid ligand is recognized by a different ligand beacon with at least a unique loop sequence and a unique fluorescent group, as described above. Measuring the fluorescence emission profile of each address on the array reveals the concentration of each target molecule.

In still further embodiments, one or more ligand beacons are attached to the solid support. Each ligand beacon can be attached via one of its termini by a spacer molecule to allow the ligand beacon to adopt the appropriate conformations without hindrance from the underlying solid support. A test mixture is contacted with one or more nucleic acid ligands, and the mixture is contacted with the solid support. Again, measurement of the fluorescent emission profile at each address of the array reveals the concentration of each target molecule in the test mixture.

The present invention also provides kits for the detection of particular targets in test mixtures. The kit comprises separate containers containing solutions of a nucleic acid ligand to the particular target, and containing solutions of the appropriate ligand beacon. In some embodiments, the kit comprises a solid support to which is attached the nucleic acid ligand to the particular target. In further embodiments, the kit further comprises a container containing a standardized solution of the target. With this solution, it is possible for the user of the kit to prepare a graph or table of fluorescence units vs. target concentration; this table or graph is then used to determine the concentration of the target in the test mixture.

EXAMPLES

Example 1
Ligand Beacon for Use with PDGF Nucleic Acid Ligand

A nucleic acid ligand to human platelet derived growth factor (PDGF) with the following sequence was obtained by the SELEX™ process:

SEQ ID NO: 1 5'-tgggagggcgcgttcttcgtggttacttttagtcccgt-3'

The sequence in bold above was used to design a ligand beacon with the following sequence:

SEQ ID NO: 2 5' gcgagaaagtaaccacgaagaagaacgcgccc ctcgc 3' wherein the bold sequence in the ligand beacon is complementary to the bold sequence in the nucleic acid ligand, and the underlined sequences form the stem.

The PDGF ligand beacon was synthesized by standard oligonucleotide chemistry with an amino linker at the 3' terminus and a fluorescein at the 5' terminus. After deprotection, the oligonucleotide was resuspended in 100 mM sodium borate buffer (pH 9.3) at 4 mg/ml, and mixed with an equal volume of the succinimidyl ester of (4-dimethylaminophenylazo)benzoic acid (DABCYL) in anhydrous N,N, dimethyl formamide (5 mg/100 µL). The reaction was allowed to proceed for 30 minutes at room temperature. Unreacted DABCYL was removed from the derivatized oligonucleotide by passing the reaction mixture through a 5000 MW cutoff Centricon filter. Subsequently, derivatized oligonucleotide was purified by gel electrophoresis under denaturing conditions. The ligand beacon was heated to 80° C. in PBSM buffer [10.1 mM $Na_2HPO_4$, 1.8 mM $KH_2PO_4$, 137 mM NaCl, 2.7 mM KCl, 1 mM $MgCl_2$, (pH 7.4)] and slowly cooled to room temperature before use.

Figure 3:
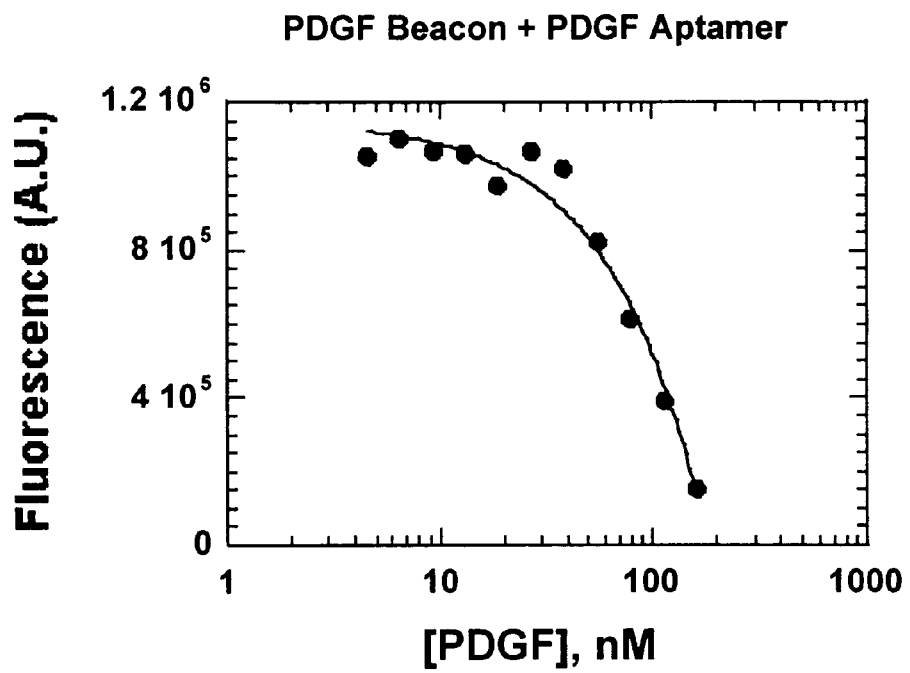
FIG. 3 illustrates that a ligand beacon that recognizes PDGF nucleic acid ligand only in the absence of the PDGF target gives a fluorescence emission signal that decreases as the concentration of PDGF increases.

The PDGF ligand beacon was used in an assay in which 100 nM PDGF nucleic acid ligand above was mixed with an increasing concentration of PDGF for 10 minutes at 30° C. polymerase in PBSM buffer containing 4 µM tRNA. Then, 100 nM PDGF ligand beacon was added and the mixture was incubated for 10 minutes at 30° C. A measurement of fluorescein emission at 530 nm was made for each concentration of PDGF using 488 nm monochromatic laser light for excitation in a 96 well format Vistra Fluorimager SI. The results are displayed in FIG. 3, wherein the X axis displays the concentration of PDGF in nanomoles and the Y axis displays fluorescein emission in arbitrary units. The results show that as the concentration of PDGF increases, the fluorescence signal decreases. This is the expected result, because as the concentration of PDGF increases, the concentration of PDGF nucleic acid ligand that is not bound to PDGF decreases. Thus, there is a smaller pool of PDGF nucleic acid ligand for the PDGF ligand beacon to hybridize to.

Example 2
Ligand Beacon for use with Nucleic Acid Ligand to TAQ Polymerase

A nucleic acid ligand to Thermophilus aquaticus (TAQ) DNA Polymerase with the following sequence was obtained through the SELEX™ methodology:

SEQ ID NO:3
5'-tggcggagcgatcatctcagagcattcttagcgttttgttcttgtgtatga-3'

The sequence in bold above was used to design a ligand beacon with the following sequence:

SEQ ID NO:4 5'-gcgagcaagaacaaaacgctaagaatgctctcgc-3'
wherein the bold sequence in the ligand beacon is complementary to the bold sequence in the nucleic acid ligand, and the underlined sequences form the stem. The ligand beacon was labeled with fluorescein at the 5' terminus and DABCYL at the 3' terminus as described in Example 1.

Figure 4:
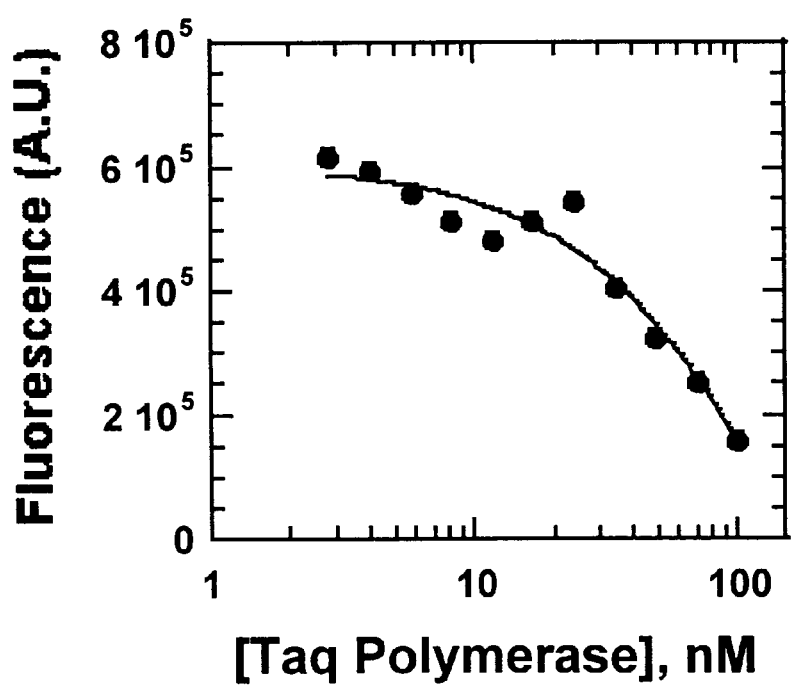
FIG. 4 illustrates the dependence of fluorescence emission on target concentration (in this case TAQ Polymerase).

An assay using constant concentrations of TAQ nucleic acid ligand and TAQ ligand beacon, and varying concentrations of TAQ DNA Polymerase, was carried out according to the method of Example 1. Again, the fluorescence emission decreased with increasing amounts of the ligand TAQ Polymerase. The results are shown in FIG. 4.

Example 3
Specificity of Ligand Beacon Interaction with Nucleic Acid Ligand

Figure 5:
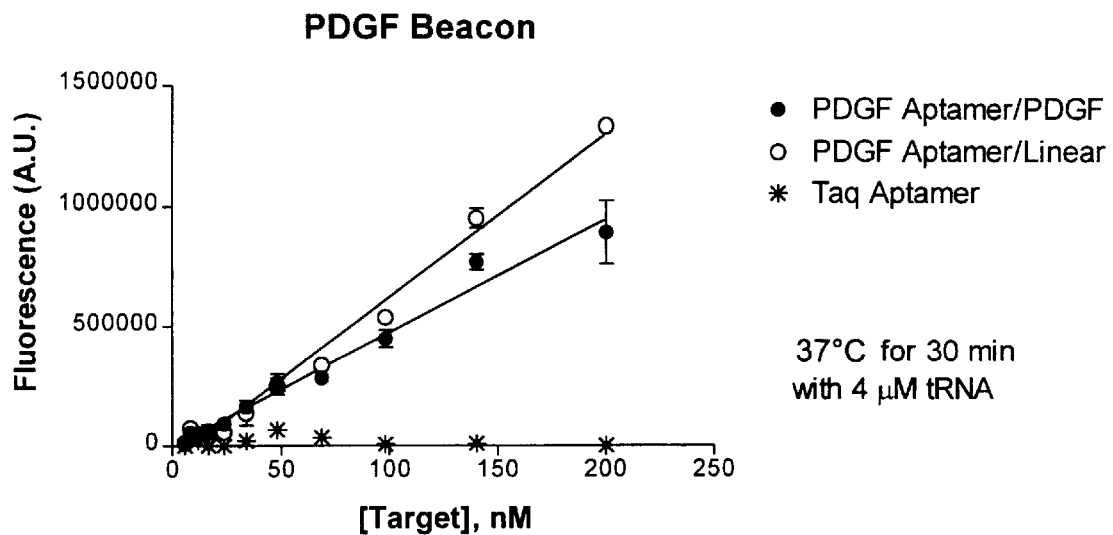
FIG. 5 illustrates that a ligand beacon, in this case a PDGF ligand beacon, binds to a complementary linear template almost as efficiently as it does to the PDGF nucleic acid ligand (aptamer). The figure also illustrates that the ligand beacon does not hybridize to a non-cognate nucleic acid ligand (a TAQ nucleic acid ligand).
Figure 6:
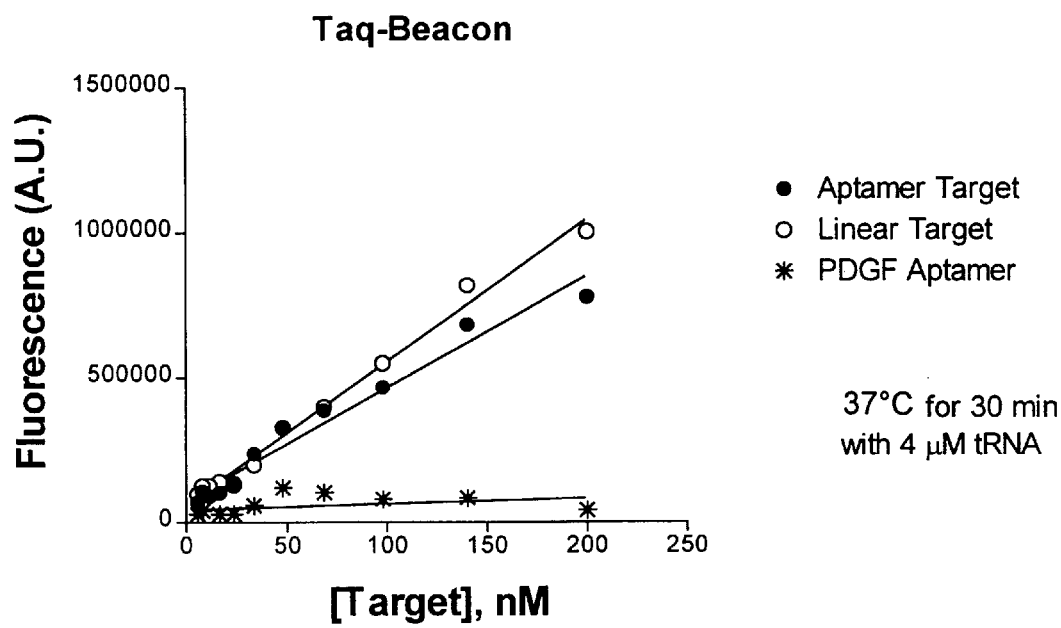
FIG. 6 illustrates that a TAQ ligand beacon binds to a complementary linear template almost as efficiently as it does to the TAQ nucleic acid ligand (aptamer). The figure also illustrates that the ligand beacon does not hybridize to a non-cognate nucleic acid ligand (a PDGF nucleic acid ligand).

In order to test the specificity of the interactions of the ligand beacons with their cognate nucleic acid ligands, the TAQ ligand beacon and the PDGF ligand beacon were contacted with either their cognate nucleic acid ligand, or a twenty nucleotides-long linear template oligonucleotide sequence that is complementary to the ligand beacon, or a non-cognate nucleic acid ligand. The results are shown in FIGS. 5 and 6. In the example shown in FIG. 5, 200 nM PDGF-ligand beacon was mixed with increasing concentration of PDGF nucleic acid ligand (closed circles), 20-nt linear PDGF template (open circle) or TAQ nucleic acid ligand (asterisks) in PBSM buffer containing 4 µM tRNA and incubated at 37° C. for 10 min before fluorescence was measured. Fluorescence was measured at 530 nm after exiting at 488 nm using monochromatic laser light in 96-well format Vistra fluorimager SI. Each experiment was done in duplicate.

In the example shown in FIG. 6, 200 nM TAQ-ligand beacon was mixed with increasing concentration of TAQ nucleic acid ligand (closed circles), 20-nt linear TAQ template (open circle) and PDGF nucleic acid ligand (asterisks) in PBSM buffer containing 4 µM tRNA and incubated at 30° C. for 10 min before fluorescence was measured. Each experiment was done in duplicate.

In both FIG. 5 and FIG. 6, open circles depict the signal when the ligand beacon met with the linear 20-nt template, whereas closed circles show the signal generated in the presence of nucleic acid ligands. In both systems the signal generated in the presence of nucleic acid ligands was somewhat lower but not all that different from the signal generated in the presence of 20-nt template. This observation suggests that ligand beacons can effectively hybridized with nucleic acid ligands at temperatures under which we typically carry out affinity selections (30° C.). When wrong combinations of nucleic acid ligand-ligand beacon pairs were mixed, virtually no fluorescence signal is generated, indicating the high degree of specificity in signal generation. This demonstrates that a multiplexed assay involving multiple nucleic acid ligand and ligand beacons is feasible. Moreover, these experiments were carried out in the presence of a vast excess of tRNA, further indicating the lack of interference on signal generation by the presence of non-specific nucleic acids.

Example 4

Figure 7:
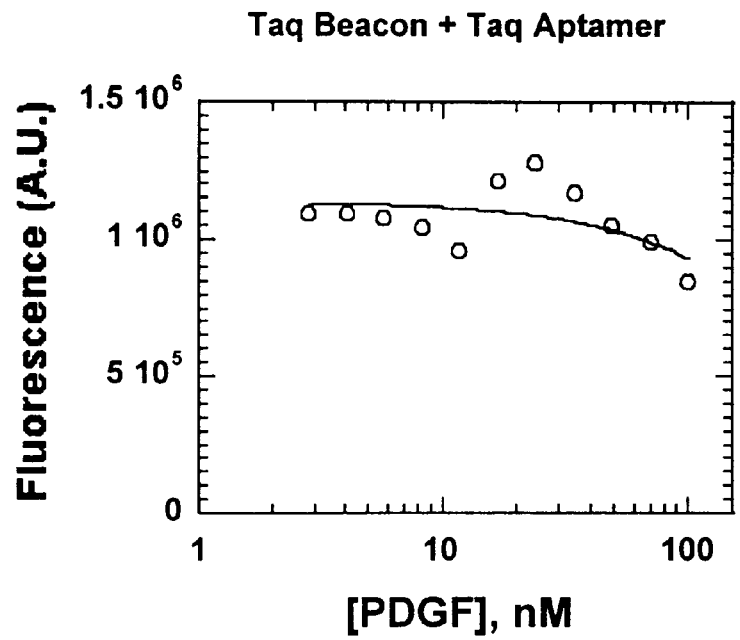
FIG. 7 illustrates the extent to which the change in fluorescence emission is dependent on the presence of a specific target. In this case, no change in fluorescence emission is observed when a nucleic acid ligand to TAQ Polymerase, and the cognate ligand beacon, are mixed with PDGF.

Specificity of Nucleic Acid Ligand Interaction with Target in the Presence of Ligand Beacon In the previous examples, a concentration-dependent signal reduction was observed when the target was added. This should not be observed when the wrong target protein is added. This point is illustrated in FIG. 7, where TAQ-nucleic acid ligand (100 nM) was mixed with increasing concentrations of PDGF in PBSM buffer containing 4 μM tRNA at 37° C. for 10 min. Then 110 nM TAQ-ligand beacon was added, incubated for an additional 10 min at the same temperature and fluorescence was measured.

The results of FIGS. 5, 6, and 7 illustrate that signal generation is specific for the target protein.

Example 5

Use of ligand beacons and nucleic acid ligands to Selectins

Ligand beacons were synthesized for P-Selectin and L-Selectin nucleic acid ligands. The sequences of the appropriate nucleic acid ligands and their cognate ligand beacons are given below:

SEQ ID NO: 5
5'-tagccaaggt aaccagtacaa ggtgctaaac gtaatggcttc ggcttac-3':
L-Selectin nucleic acid ligand
SEQ ID NO: 6
5'-Fgcgagtgtac tggttaccttt ggctactcg cD-3'
L-Selectin ligand beacon
SEQ ID NO: 7
5'-cucaacgagc caggaacauc gaggucagca aacgcgag-3'
P-Selectin nucleic acid ligand
SEQ ID NO: 8
5'-Fgcgagctcgc gtttgctgac gtcgactcg cD-3'
P-Selectin ligand beacon wherein the L-Selectin nucleic acid ligand is a 49-mer single-stranded DNA, and the P-Selectin nucleic acid ligand is a 38-mer RNA molecule containing 2° F-substituted pyrimidines. The F represents fluorescein, and D represents DABCYL. As in the previous examples, the ligand beacons were synthesized with fluorescein at the 5' end, and a free amino group at the 3' end. The free amino group was reacted with the succinimidyl ester of DABCYL in order to position DABCYL at the 3' end of the ligand beacon.

Figure 8:
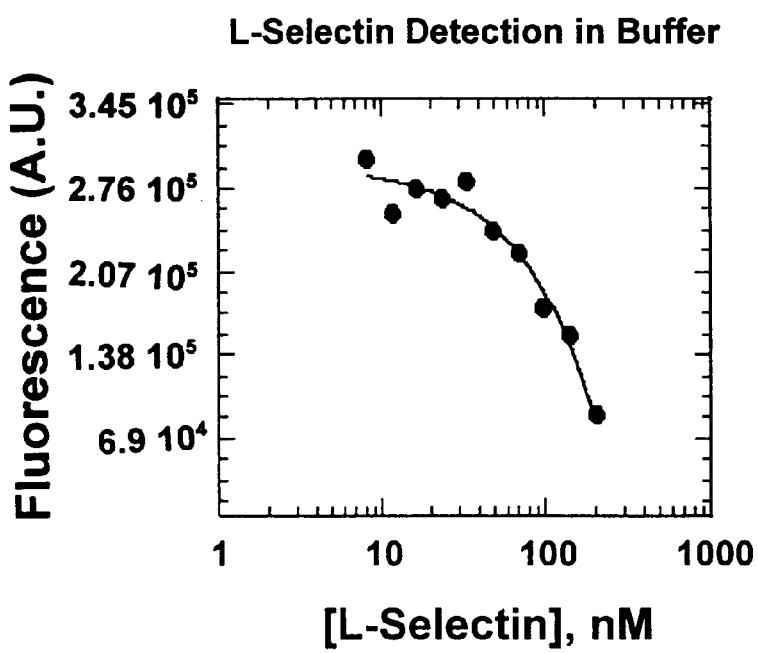
FIG. 8 illustrates the dependence of fluorescence emission on target concentration using a nucleic acid ligand to L-Selectin and the cognate ligand beacon.
Figure 9:
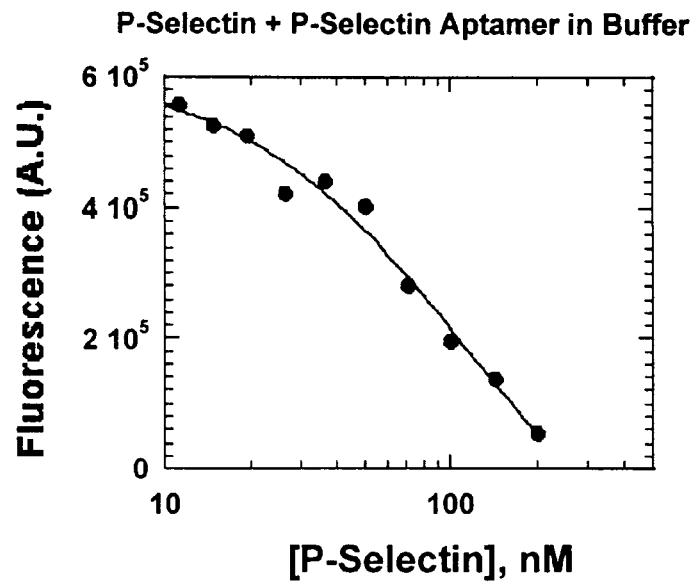
FIG. 9 illustrates the dependence of fluorescence emission on target concentration using a nucleic acid ligand to P-Selectin and the cognate ligand beacon.

As shown in FIG. 8, L-Selectin nucleic acid ligand (200 nM) was mixed with increasing concentrations of L-Selectin in SHMCK buffer containing 4 μM tRNA at 37° C. for 15 min. Then 220 nM L-Selectin-Beacon was added, incubated for an additional 10 min at the same temperature and fluorescence was measured. The observed fluorescence signal was plotted against the corresponding concentration of L-Selectin. As depicted in FIG. 9, P-Selectin nucleic acid ligand (200 nM) was mixed with increasing concentration of P-Selectin in SHMCK buffer containing 4 μM tRNA at 37° C. for 15 min. Then 220 nM P-Selectin-Beacon was added, incubated for an additional 10 min. at the same temperature and fluorescence was measured. The observed fluorescence signal was plotted against the corresponding concentration of P-Selectin. In both experiments, the intensity of the fluorescence signal decreased with the increase in Selectin concentration.

Figure 10:
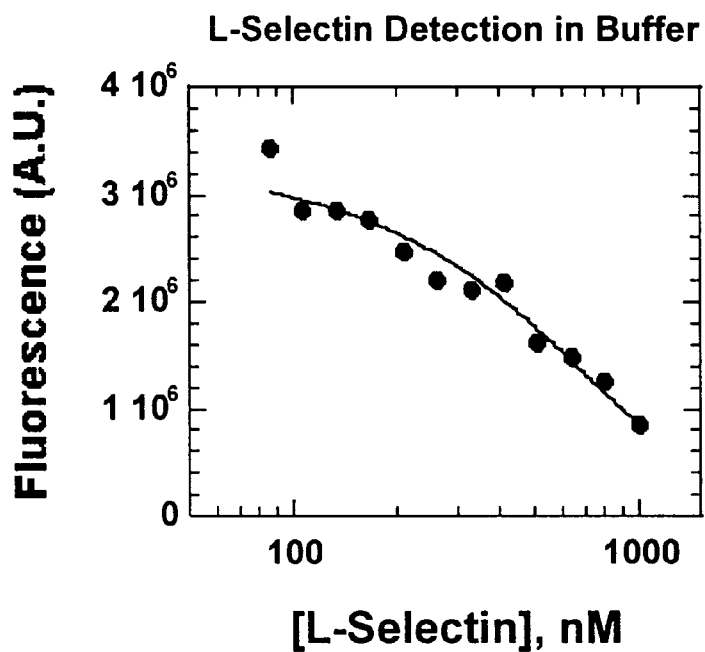
FIG. 10 further illustrates the dependence of fluorescence emission on target concentration using a nucleic acid ligand to L-Selectin and the cognate ligand beacon. A higher concentration of nucleic acid ligand and ligand beacon were used than in FIG. 9. The fluorescence emission data show that the dynamic range of ligand beacon assays can be varied by changing the concentration of nucleic acid ligand and ligand beacon in an assay.

L-Selectin nucleic acid ligand (800 nM) was mixed with increasing concentration of L-Selectin in SHMCK buffer containing 4 μM tRNA at 37° C. for 15 min. The results are shown in FIG. 10. The concentrations used here were higher than those used in the example shown in FIG. 9. Then 800 nM L-Selectin-ligand beacon was added, incubated for an additional 10 min at the same temperature and fluorescence was measured. The observed fluorescence signal was plotted against the corresponding concentration of L-Selectin. It can be seen that the dynamic range of the assay can be easily varied by changing the concentration of the nucleic acid ligand/ligand beacon pair.

Example 6

Figure 11:
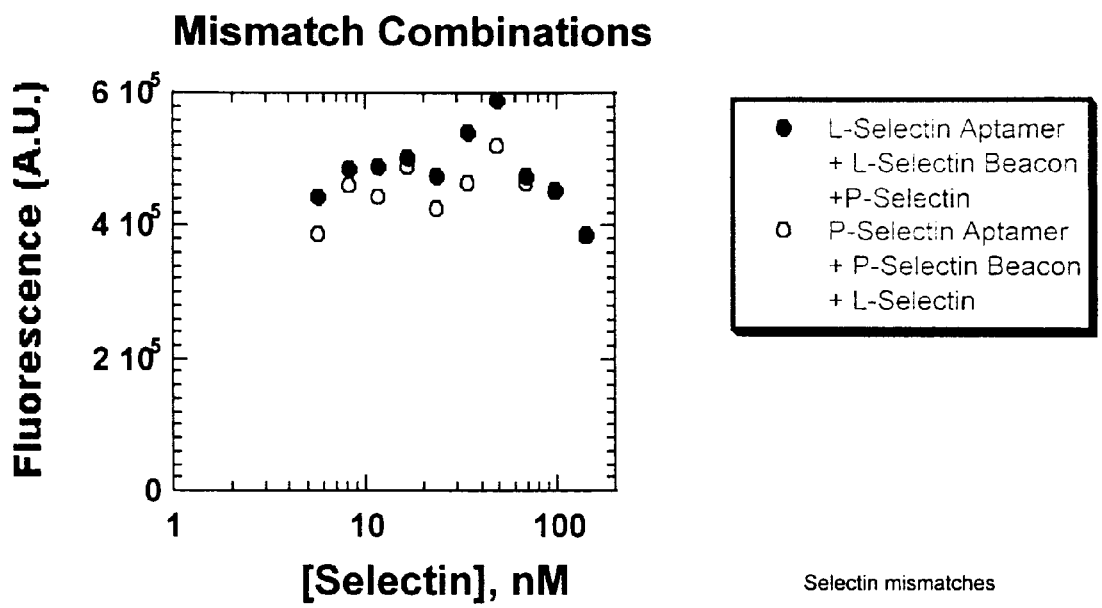
FIG. 11 illustrates that a change in fluorescence emission occurs only when a nucleic acid ligand meets its cognate target and not when in the presence of a homologous target.

Interaction of the Ligand Beacon with Nucleic Acid Ligands to Homologous Proteins In order to demonstrate the specificity of the ligand beacon/nucleic acid ligand interaction, an assay was performed in which the P-Selectin nucleic acid ligand was mixed with its cognate ligand beacon and L-Selectin. Specifically, L-Selectin nucleic acid ligand (200 nM) was mixed with increasing concentrations of P-Selectin in SHMCK buffer containing 4 μM tRNA. The mixture was incubated at 37° C. for 15 min. Then 220 nM L-Selectin-Beacon was added, incubated additional 10 min at the same temperature and fluorescence was measured (FIG. 11 closed circles). Then, P-Selectin nucleic acid ligand was mixed with its cognate ligand beacon and L-Selectin. Specifically, P-Selectin nucleic acid ligand (200 nM) was mixed with increasing concentrations of L-Selectin in SHMCK buffer containing 4 μM tRNA at 37° C. for 15 min. Then 220 nM P-Selectin-Beacon was added, incubated for an additional 10 min at the same temperature and fluorescence was measured (FIG. 11; open circles).

As can be seen from the results shown in FIG. 11, there is a little or no change in the fluorescence intensity when the wrong Selectin is added. In the presence of the wrong target protein the nucleic acid ligand is available for binding to the ligand beacon resulting in high fluorescence. This result indicates that the change in fluorescence is dependent on the presence of the specific target.

Example 7

Use of Ligand Beacons in Plasma

Figure 12:
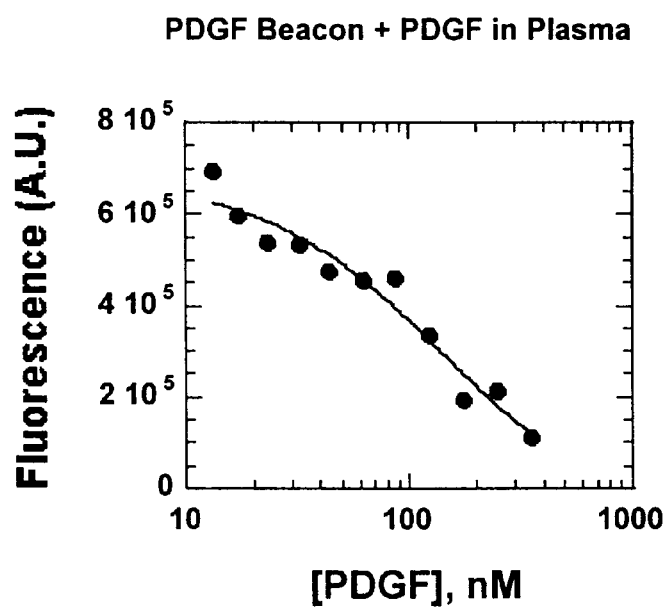
FIG. 12 illustrates the use of ligand beacons in a PDGF assay in human plasma.

The results of a ligand beacon assay for detecting PDGF in human plasma are illustrated in FIG. 12. In this assay, PDGF nucleic acid ligand (100 nM) was mixed with increasing concentrations of PDGF in human plasma containing 4 μM tRNA. The mixture was incubated at 37° C. for 15 min. Then 110 nM PDGF-Beacon was added, incubated for an additional 10 min at the same temperature and fluorescence was measured. The observed fluorescence signal was plotted against the corresponding concentration of PDGF.

Figure 13:
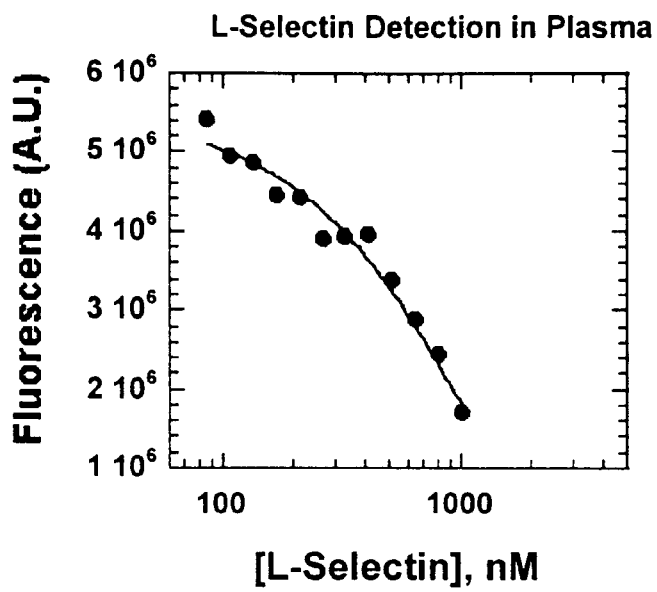
FIG. 13 illustrates that ligand beacons can be used to detect L-Selectin in human plasma.

The results of a ligand beacon assay for detecting L-Selectin in human plasma are illustrated in FIG. 13. In this assay, L-Selectin nucleic acid ligand (800 nM) was mixed with increasing concentrations of L-Selectin in human plasma containing 4 μM tRNA. The mixture was incubated at 37° C. for 15 min. Then 800 nM L-Selectin-Beacon was added, incubated for an additional 10 min at the same temperature and fluorescence was measured. The observed fluorescence signal was plotted against the corresponding concentration of L-Selectin.

Figure 14:
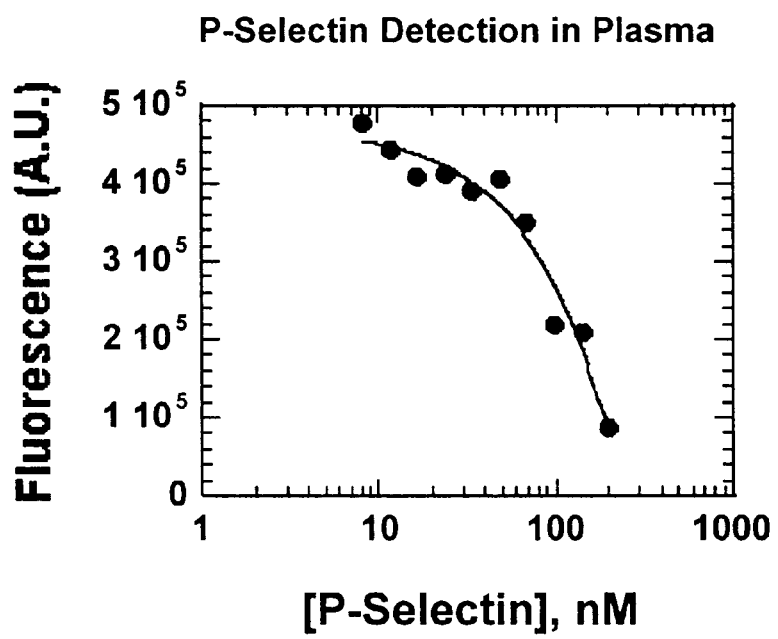
FIG. 14 illustrates that ligand beacons can be used to detect P-Selectin in human plasma.

The results of a ligand beacon assay for detecting P-Selectin in human plasma are illustrated in FIG. 14. L-Selectin nucleic acid ligand (100 nM) was mixed with increasing concentrations of P-Selectin in human plasma containing 4 $\mu$M tRNA. The mixture was incubated at 37° C. for 15 min. Then 100 nM P-Selectin-Beacon was added, incubated for an additional 10 min at the same temperature and fluorescence was measured. The observed fluorescence signal was plotted against the corresponding concentration of P-Selectin.

These three examples demonstrate that ligand beacons can be successfully used with plasma.

What is claimed is:

1. A nucleic acid ligand:ligand beacon complex comprised of a nucleic acid ligand and a ligand beacon comprised of i) a nucleic acid sequence complementary to at least a portion of said nucleic acid ligand; ii) a fluorescent group; and iii) a fluorescence modifying group.

2. The nucleic acid ligand:ligand beacon complex of claim 1 wherein said fluorescence-modifying group is a quenching group.

3. The nucleic acid ligand:ligand beacon complex of claim 2 wherein said quenching group is (4-dimethlyaminophenylazo) benzoic acid (DABCYL).

4. The nucleic acid ligand:ligand beacon complex of claim 1 wherein said fluorescent group is selected from the group consisting of fluorescein, tetramethylrhodamine, 5-[(2-aminoethyl)amino]napthalene-1-sulfonic acid (EDANS), Texas Red, BODIPY, Lucifer yellow, and coumarin.

* * * * *

SEQUENCE LISTING

<160> NUMBER OF SEQ ID NOS: 8

<210> SEQ ID NO 1
<211> LENGTH: 38
<212> TYPE: DNA
<213> ORGANISM: Artificial Sequence
<220> FEATURE:
<223> OTHER INFORMATION: Description of Artificial Sequence:
      Nucleic Acid Ligand to Platelet Derived Growth Factor (PDGF)

<400> SEQUENCE: 1
tgggagggcg cgttcttcgt ggttactttt agtcccgt                              38

<210> SEQ ID NO 2
<211> LENGTH: 37
<212> TYPE: DNA
<213> ORGANISM: Artificial Sequence
<220> FEATURE:
<223> OTHER INFORMATION: Description of Artificial Sequence:
      Ligand Beacon to PDGF Nucleic Acid Ligand of SEQ ID NO:1
<221> NAME/KEY: misc_feature
<222> LOCATION: (1)
<223> OTHER INFORMATION: 5' Fluorescein
<221> NAME/KEY: misc_feature
<222> LOCATION: (37)
<223> OTHER INFORMATION: 3' (4-dimethylaminophenylazo) benzoic acid
      (DABCYL)
<221> NAME/KEY: stem_loop
<222> LOCATION: (1)..(37)

<400> SEQUENCE: 2
gcgagaaagt aaccacgaag aagaacgcgc ccctcgc                               37

<210> SEQ ID NO 3
<211> LENGTH: 51
<212> TYPE: DNA
<213> ORGANISM: Artificial Sequence
<220> FEATURE:
<223> OTHER INFORMATION: Description of Artificial Sequence:
      Nucleic Acid Ligand to Thermophilus aquaticus (TAQ)  DNA
      Polymerase

<400> SEQUENCE: 3
tggcggagcg atcatctcag agcattctta gcgttttgtt cttgtgtatg a              51

<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence:
      Ligand Beacon to TAQ Polymerase  Nucleic Acid Ligand of SEQ ID
      NO:3
<221> NAME/KEY: misc_feature
<222> LOCATION: (1)
<223> OTHER INFORMATION: 5' Fluorescein
<221> NAME/KEY: misc_feature
<222> LOCATION: (34)

```
<223> OTHER INFORMATION: 3' (4-dimethylaminophenylazo) benzoic acid
      (DABCYL)
<221> NAME/KEY: stem_loop
<222> LOCATION: (1)..(34)

<400> SEQUENCE: 4
gcgagcaaga acaaaacgct aagaatgctc tcgc                              34

<210> SEQ ID NO 5
<211> LENGTH: 49
<212> TYPE: DNA
<213> ORGANISM: Artificial Sequence
<220> FEATURE:
<223> OTHER INFORMATION: Description of Artificial Sequence:
      Nucleic Acid Ligand to L-Selectin

<400> SEQUENCE: 5
tagccaaggt aaccagtaca aggtgctaaa cgtaatggct tcggcttac              49

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence:
      Ligand Beacon to L-Selectin Nucleic Acid Ligand of SEQ ID NO:5
<221> NAME/KEY: misc_feature
<222> LOCATION: (1)
<223> OTHER INFORMATION: 5' Fluorescein
<221> NAME/KEY: misc_feature
<222> LOCATION: (30)
<223> OTHER INFORMATION: 3' (4-dimethylaminophenylazo) benzoic acid
      (DABCYL)
<221> NAME/KEY: stem_loop
<222> LOCATION: (1)..(30)

<400> SEQUENCE: 6
gcgagtgtac tggttacctt ggctactcgc                                   30

<210> SEQ ID NO 7
<211> LENGTH: 38
<212> TYPE: RNA
<213> ORGANISM: Artificial Sequence
<220> FEATURE:
<223> OTHER INFORMATION: Description of Artificial Sequence:Nucleic Acid
      Ligand to P-Selectin
<221> NAME/KEY: modified_base
<222> LOCATION: (1)..(38)
<223> OTHER INFORMATION: C, U are 2' F

<400> SEQUENCE: 7
cucaacgagc caggaacauc gaggucagca aacgcgag                          38

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence:
      Ligand Beacon to P-Selectin Nucleic Acid Ligand of SEQ ID NO:7
<221> NAME/KEY: misc_feature
<222> LOCATION: (30)
<223> OTHER INFORMATION: 3' (4-dimethylaminophenylazo) benzoic acid
      (DABCYL)
<221> NAME/KEY: stem_loop
<222> LOCATION: (1)..(30)

<400> SEQUENCE: 8
gcgagctcgc gtttgctgac gtcgactcgc                                   30
```